(12) United States Patent
Farah

(10) Patent No.: US 12,226,263 B2
(45) Date of Patent: Feb. 18, 2025

(54) METHOD OF PRODUCING AN INTERLOCKED STRUCTURE

(71) Applicant: SENSO MEDICAL LABS LTD., Nazareth (IL)

(72) Inventor: Maroun Farah, Nazareth (IL)

(73) Assignee: SENSO MEDICAL LABS LTD., Nazareth (IL)

( * ) Notice: Subject to any disclaimer, the term of this patent is extended or adjusted under 35 U.S.C. 154(b) by 1208 days.

(21) Appl. No.: 16/936,609

(22) Filed: Jul. 23, 2020

(65) Prior Publication Data

US 2020/0345447 A1 Nov. 5, 2020

Related U.S. Application Data

(63) Continuation of application No. 15/525,294, filed as application No. PCT/IL2015/051080 on Nov. 9, 2015, now Pat. No. 10,751,143.

(Continued)

(51) Int. Cl.
*A61B 90/11* (2016.01)
*A61B 17/00* (2006.01)
(Continued)

(52) U.S. Cl.
CPC ........ *A61B 90/11* (2016.02); *A61B 17/00234* (2013.01); *A61B 34/10* (2016.02); *A61B 90/14* (2016.02); *A61B 90/39* (2016.02); *A61C 1/082* (2013.01); *A61N 1/04* (2013.01); *A61N 1/0534* (2013.01); *A61N 1/0551* (2013.01); *D03D 15/533* (2021.01); *A61B 2017/00946* (2013.01); *A61B 2034/105* (2016.02); *A61B 2034/107* (2016.02); *A61B 2034/108* (2016.02); *A61B 34/30* (2016.02); *A61B 2090/363* (2016.02);
(Continued)

(58) Field of Classification Search
CPC ....... A61B 5/287; A61B 5/0538; A61B 5/282; A61B 18/24; A61B 2018/1467; A61B 17/12168; A61B 2017/1205; A61B 2562/125; A61B 90/11; Y10T 29/49117; Y10T 29/49002
USPC .............. 29/592.1, 605, 825, 874, 882, 92.1
See application file for complete search history.

(56) References Cited

U.S. PATENT DOCUMENTS 5,311,866 A 5/1994 Kagan et al.
5,330,524 A 7/1994 Mar
(Continued)

FOREIGN PATENT DOCUMENTS

CA 2 447 239 C 10/2010
CA 2 751 569 C 3/2015
(Continued)

*Primary Examiner* — Thiem D Phan

(57) ABSTRACT

An electrode lead is provided having a distal side and a circumferential surface, the electrode lead comprising a plurality of interlocked filaments having a conductive core coated with a nonconductive coating and at least one 3D distinct conductive mass at the distal end, wherein the filaments in the conductive mass are having an exposed conductive core and wherein a portion of the filaments with the exposed conductive core are disposed on the circumferential surface. The 3d pattern of spaced-apart regions along or within the electrode lead, each one is a network of spaced-apart conductive segments determining together critical parameters of: directionality of the region and electrical property of the region.

21 Claims, 12 Drawing Sheets

Related U.S. Application Data

(60) Provisional application No. 62/077,247, filed on Nov. 9, 2014.

(51) Int. Cl.
    *A61B 34/10*     (2016.01)
    *A61B 90/00*     (2016.01)
    *A61B 90/14*     (2016.01)
    *A61C 1/08*     (2006.01)
    *A61N 1/04*     (2006.01)
    *A61N 1/05*     (2006.01)
    *D03D 15/533*     (2021.01)
    *A61B 34/30*     (2016.01)

(52) U.S. Cl.
    CPC .......... *A61N 1/05* (2013.01); *Y10T 29/49002* (2015.01); *Y10T 29/49201* (2015.01)

(56) References Cited

U.S. PATENT DOCUMENTS

| | | | |
|---|---|---|---|
| 7,097,451 B2 | 8/2006 | Tang | |
| 7,470,483 B2 | 12/2008 | Yoshida et al. | |
| 7,651,506 B2 | 1/2010 | Bova et al. | |
| 7,722,604 B2 * | 5/2010 | Brown, III | A61M 25/0136 606/41 |
| 7,835,778 B2 | 11/2010 | Foley et al. | |
| 8,504,132 B2 * | 8/2013 | Friedman | A61B 5/287 600/509 |
| 8,923,984 B2 | 12/2014 | Parker et al. | |
| 10,085,784 B2 | 10/2018 | Ono et al. | |
| 2004/0131920 A1 | 7/2004 | Yoshida et al. | |
| 2007/0106357 A1 | 5/2007 | Denker et al. | |
| 2007/0190881 A1 | 8/2007 | Shibaoka et al. | |
| 2008/0166681 A1 | 7/2008 | Weinstein et al. | |
| 2008/0196783 A1 | 8/2008 | Van Bruggen et al. | |
| 2010/0070008 A1 | 3/2010 | Parker et al. | |
| 2012/0232629 A1 | 9/2012 | Bloemer et al. | |
| 2014/0288577 A1 | 9/2014 | Robinson et al. | |
| 2014/0324143 A1 | 10/2014 | Robinson et al. | |
| 2019/0160279 A1 | 5/2019 | Farah | |

FOREIGN PATENT DOCUMENTS

| | | |
|---|---|---|
| CN | 103230302 A | 8/2013 |
| CN | 103157181 B | 7/2015 |
| CN | 107106838 A | 8/2017 |
| CN | 109475300 A | 3/2019 |
| DE | 102008040773 A1 | 2/2010 |
| EP | 1094760 B1 | 3/2006 |
| EP | 1 731 643 A1 | 12/2006 |
| EP | 3215215 A2 | 9/2017 |
| EP | 3454726 A1 | 1/2020 |
| JP | 2000-221 A | 1/2000 |
| JP | 2008-542565 A | 11/2008 |
| JP | 2011-15818 A | 1/2011 |
| JP | 5487496 B2 | 5/2014 |
| WO | 2008/048237 A2 | 4/2008 |
| WO | 2010/033370 A2 | 3/2010 |
| WO | 2010/117381 A1 | 10/2010 |
| WO | 2013/075171 A1 | 5/2013 |
| WO | 2013/075178 A1 | 5/2013 |
| WO | 2014/176118 A1 | 10/2014 |

\* cited by examiner

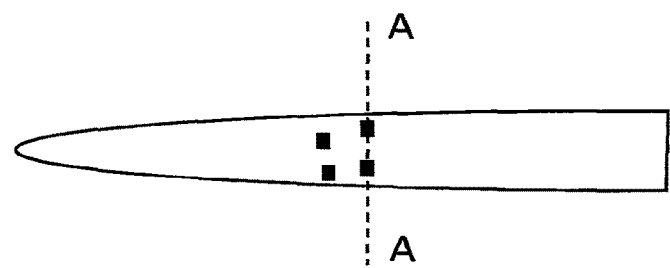
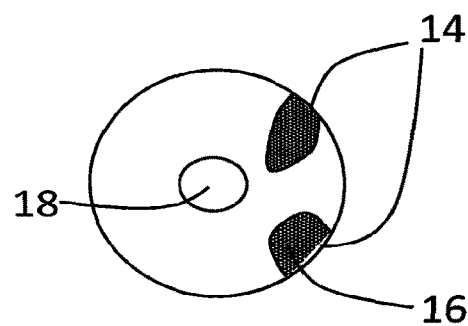
Figure 1a
Figure 1b
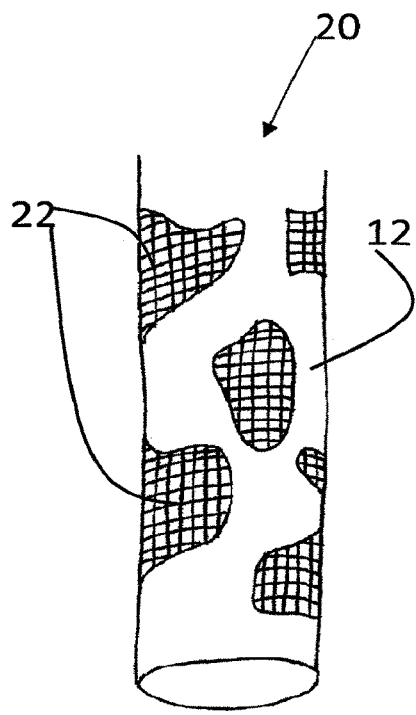
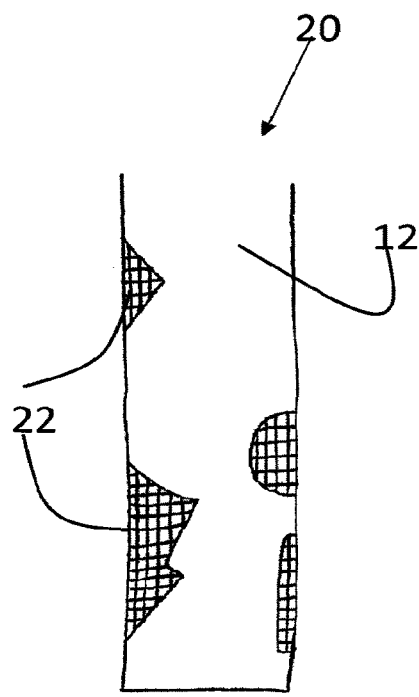
Figure 1c
Figure 1d

METHOD OF PRODUCING AN INTERLOCKED STRUCTURE

CROSS-REFERENCE TO RELATED APPLICATIONS

This application is a continuation of U.S. application Ser. No. 15/525,294 filed on May 9, 2017, which is a national stage application under 35 U.S.C. § 371 of PCT/IL2015/051080 filed on Nov. 9, 2015 and subsequently published as WO/2016/071916 on May 12, 2016, said PCT application claiming the benefit of U.S. provisional application 62/077,247, filed Sep. 11, 2014 according to 35 U.S.C. § 119 (e). Each of these earlier applications is fully incorporated herein by reference.

FIELD OF THE INVENTION

The invention relates to electrode leads that can be used for sensing or stimulating electrical impulses in tissues and methods of producing same.

BACKGROUND OF INVENTION

Electrical stimulation of bodily parts such as spinal cord, peripheral nerves, cranial nerves, nerve roots, muscles, or brain issues is used to treat various conditions including, for example, Parkinson's disease, dystonia, chronic pain, Huntington's disease, bradykinesia, epilepsy and seizures, eating disorders, and mood disorders. For those conditions as well as others, sensing or recording electrodes arm also available for monitoring the electrical activity of the tissues to be treated or studied. Many of the electrodes, whether stimulating or sensing electrodes, have similar characteristics.

Typically, an electrode for stimulation comprises a flexible, axially extending probe body with several annular other structural stimulation contacts distributed at equal or different distances along a region of the probe body. Similar electrodes can be built for recording physiological potentials and neural activity in those tissues, especially brain tissues.

While optimizing stimulation of the electrodes based on therapeutic results, a finer shaping of the electrical field formed by the electrode is required, which in turn will shape an activating field (the activation field is the actual area in the brain being affected by neuronal elements being activated and or inhibited by produced electrical field). By directing the activation field towards desired tissue region and limiting its extent from other regions, much better optimization can be performed, while increasing the therapeutic benefit to the patient and decreasing the side effects from the stimulation as partially done with today's technologies only along the electrode lead and not in directions perpendicular to the lead axis. Optimizing the shape of the activation field requires, among other, to increase the number and resolution of the electrode contacts so as to increase the resolution of the activation field that can be accomplished. Therefore, the directionality of the electrode contacts is very important.

Currently marketed electrodes contain limited number of contacts; these electrodes are assembled manually or in a semi-automatic manner. Future approaches are directed towards other methods of electrode lead manufacturing like lithographic etching, electroforming, laser ablation and other to precisely manufacture electrode arrays with finer contacts and higher number of contacts. However, these methods are cumbersome and the procedure is relatively long and as a rule, have limited and essentially two-dimensional surfaces, As the contact surface is smaller, the area contacting the body fluid or body tissue becomes smaller as well and the electrical properties of the electrode are worsens (e.g. impedance of contact increases), resulting in potentially high current densities that might be harmful. It is extremely difficult to produce arrays of small electrodes having complex shapes with a large number of conductive surfaces, in particular asymmetric arrays that can be crucial in treating conditions as mentioned.

U.S. Pat. No. 5,330,524 discloses an implantable cardiac defibrillation electrode, in which there is an electrically conductive wire mesh formed of crossed spirally wound cables. Each of the spirally wound cables includes a plurality of stranded wire elements, with a central wire element and a plurality of outer wire elements wound adjacent to the central wire element. Such electrodes do provide flexibility and a large contact surface area; however, the meshes described in U.S. 5,330,524 are electrically conductive in their entirety, but am not sufficiently directional or area-specific for some applications.

Another example is described by Parker at al, in U.S. Pat. No. 8,923,984. The disclosure depicts neurostimulator made of a knitted electrode. In this case, there is a possibility to form contact areas that are more specific since a conductive filament is intertwined within non-conductive filaments. Among other disadvantages of the disclosed structure, the knitted electrode has relative large spacing between adjacent rows, a fact that prevents accurate and stable positioning of the electrode in a desired area that is usually very small.

The present invention, on the other hand, aims at addressing the need for more specificity in controlling the size and positioning of the very small contacts on the electrode lead according to an aspect of the invention as well as their critical properties their directionality and their electrical properties (e.g. impedance). The electrode lead according to the present invention is easily and accurately fabricated.

SUMMARY OF THE INVENTION

It is therefore provided in accordance with one aspect, an electrode lead having a distal side and a circumferential surface, the electrode lead comprising:
  a plurality of interlocked filaments having a conductive core coated with a nonconductive coating:
  at least one 3D distinct conductive mass at the distal end, wherein the filaments in the conductive mass are having an exposed conductive core and wherein a portion of the filaments with the exposed conductive core are disposed on the circumferential surface.

It is therefore provided in accordance with one aspect, an electrode lead having a distal side and a circumferential surface, the electrode lead comprising:
  3d pattern of spaced-apart regions along or within the electrode lead, each one of said spaced-apart regions is a network of spaced-apart conductive segments determining together critical parameters of: directionality of the region and electrical property of the region.

According to another embodiment, the conductive core of the filaments in the conductive mass are extended to a proximal end of the electrode lead and are connected to an electronic module.

According to another embodiment, the interlocked filaments are interlocked using one of the methods such as braiding, knitting, weaving, interwinding, entangling, or meshing.

According to another embodiment, said plurality of interlocked filaments am arranged in layers.

According to another embodiment, said layers are axial.

According to another embodiment, electrical signals can be transferred through the conductive mass to or from the electronic module.

According to another embodiment, the electrode lead is provided with at least one insert resides in between layers that comprise the electrode lead, and wherein filaments are passed through at least one slot in the insert in an angle relative to an elongated axis of the electrode lead.

According to another embodiment, the filaments are cut at the circumferential surface.

According to another embodiment, the insert can be positioned as an inner most layer.

According to another embodiment, the insert is extending only partially in the electrode lead.

According to another aspect, a method is provided of producing an electrode lead comprising:
  providing a machine capable of interlocking a plurality of filaments into a 3D structure;
  providing a plurality of filaments, a portion of the filaments are nonconductive filaments and another portion of filaments comprising a conductive core coated with a nonconductive coating;
  providing a laser capable of directing a laser beam towards the filaments during interlocking;
  interlocking said plurality of filaments according to a premeditated program to form said 3D structure;
  directing said laser beam to a one of said another portion of filaments so as to expose said conductive core during said interlocking said plurality of filaments.

According to another embodiment, said 3D structure is the electrode lead as described before.

According to another embodiment, the method further comprising providing a dispenser capable of directing material towards the filaments during interlocking and dispensing said material onto the plurality of filaments during said interlocking said plurality of filaments.

According to another embodiment, said machine is provided with a hollow cylinder onto which the 3D structure is interlocked.

According to another embodiment, the cylinder is provided with at least one slot through which additional filaments can be transferred from the hollow to outside the 3D structure.

According to another embodiment, the method further comprising pulling the additional filaments from the hollow through the slot in a direction opposite to the direction of said interlocking said plurality of filament.

According to another embodiment, the method further comprising cutting the additional filament adjacent to the circumferential surface.

According to another embodiment, wherein said machine is provided with a weaver having a rotating cylinder onto which the 3D structure is interlocked.

According to another embodiment, said laser is incorporated within said weaver.

According to another embodiment, the method further comprising providing a computing module and programming the computing module to instruct the machine according to a predetermined pattern of the 3D structure.

According to another embodiment, said programming the computing module comprises providing parameters from which characteristics of the electrode lead are established.

According to another embodiment, said programming the computing module comprises providing characteristics of the electrode lead from which parameters of said interlocking the plurality of filaments are established.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention, in this regard, no attempt is made to show structural details of the invention in more detail than is necessary for a fundamental understanding of the invention, the description taken with the drawings making apparent to those skilled in the art how the several forms of the invention may be embodied in practice.

The present invention will be understood and appreciated more fully from the following detailed description, taken in conjunction with the drawings in which:

Figure 2A:
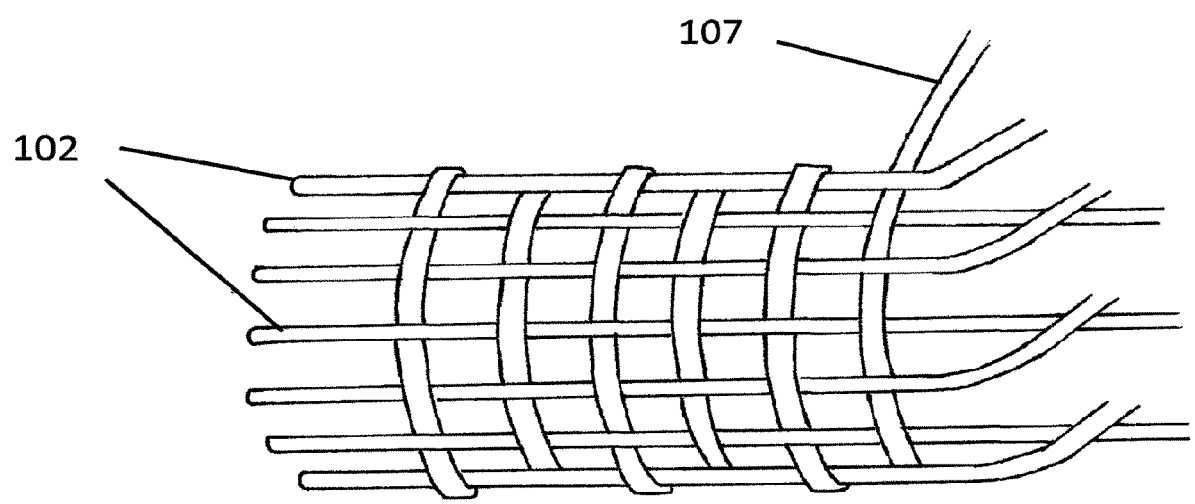

While the disclosure is amenable to various modifications and alternative forms, specifics thereof have been shown by way of example in the drawings and will be further described in detail herein below. It should be understood, however, that the intention is not to limit the disclosure to the particular embodiments described. On the contrary, the intention is to cover all modifications, equivalents, and alternatives.

FIG. 1a illustrates a schematic drawing of distal portion of an electrode lead according to an exemplary embodiment.

FIG. 1b illustrates a schematic cross sectional view of the electrode lead shown in FIG. 1a.

FIG. 1c illustrates a schematic drawing of distal portion of an electrode lead according to another exemplary embodiment.

FIG. 1d illustrates a schematic drawing of a cross section distal portion of an electrode lead along its axial axis.

FIG. 2a schematically illustrates a method of weaving layered lead in accordance with exemplary embodiment.

Figure 2B:
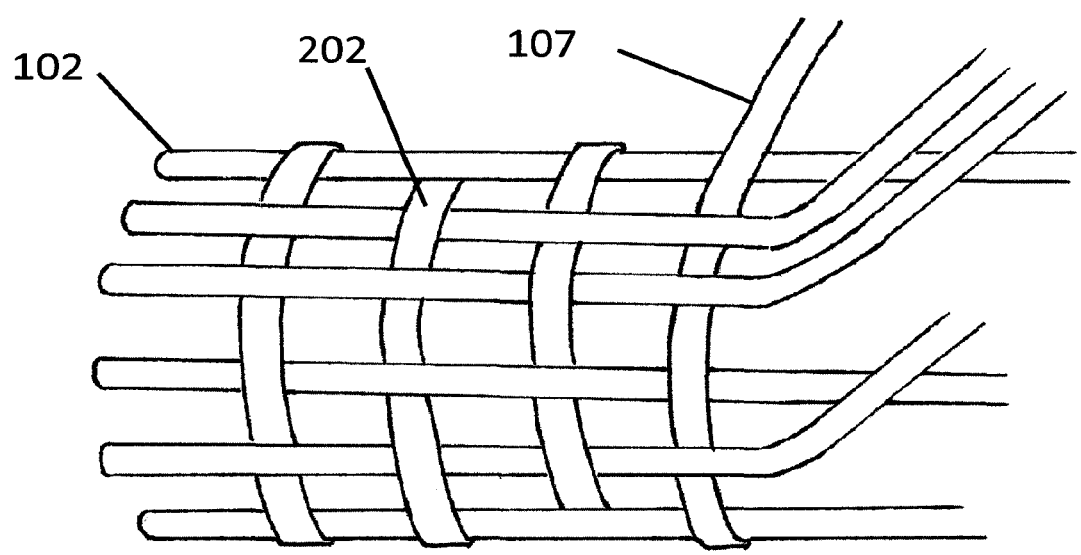

FIG. 2b schematically illustrates method of weaving layered lead in accordance with another exemplary embodiment.

Figure 2C:
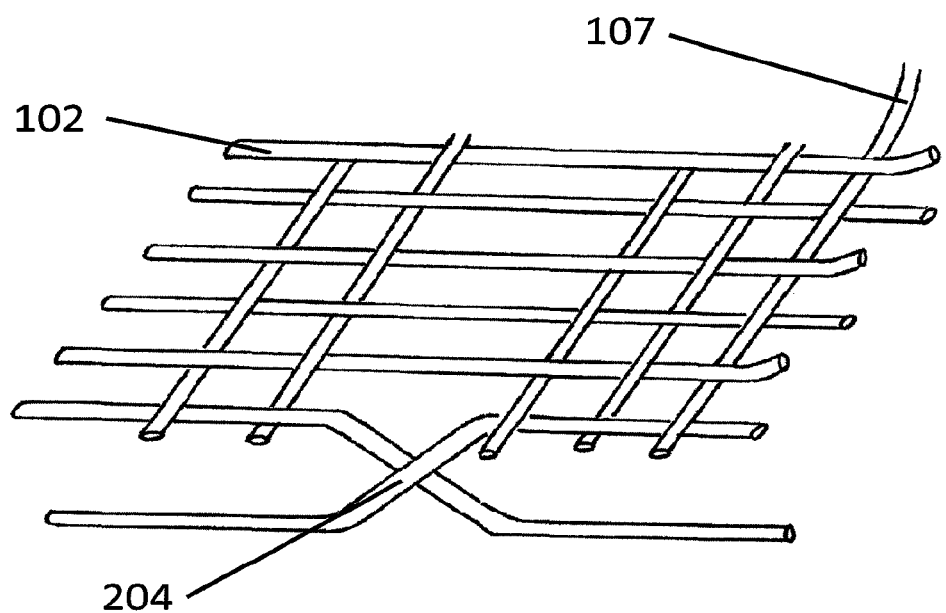

FIG. 2c schematically illustrates method of weaving layered lead in accordance with another exemplary embodiment.

Figure 2D:
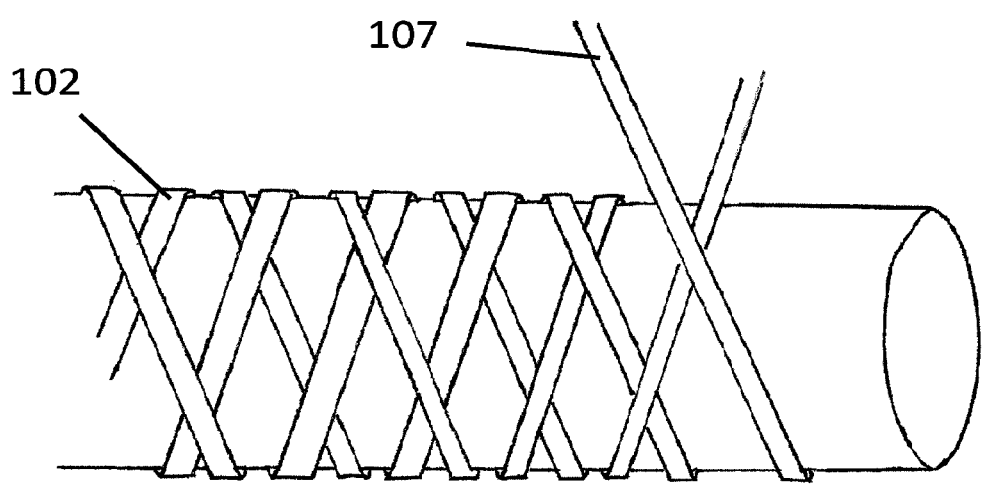

FIG. 2d schematically illustrates method of weaving layered lead in accordance with another exemplary embodiment.

Figure 2E:
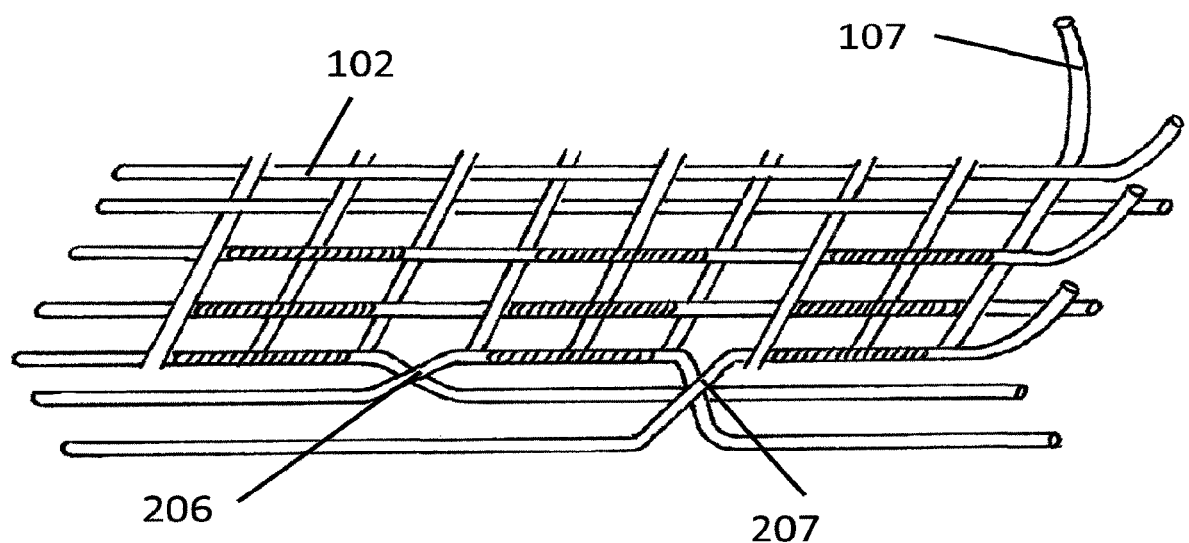

FIG. 2e schematically illustrates method of weaving layered lead in accordance with another exemplary embodiment.

Figure 3:
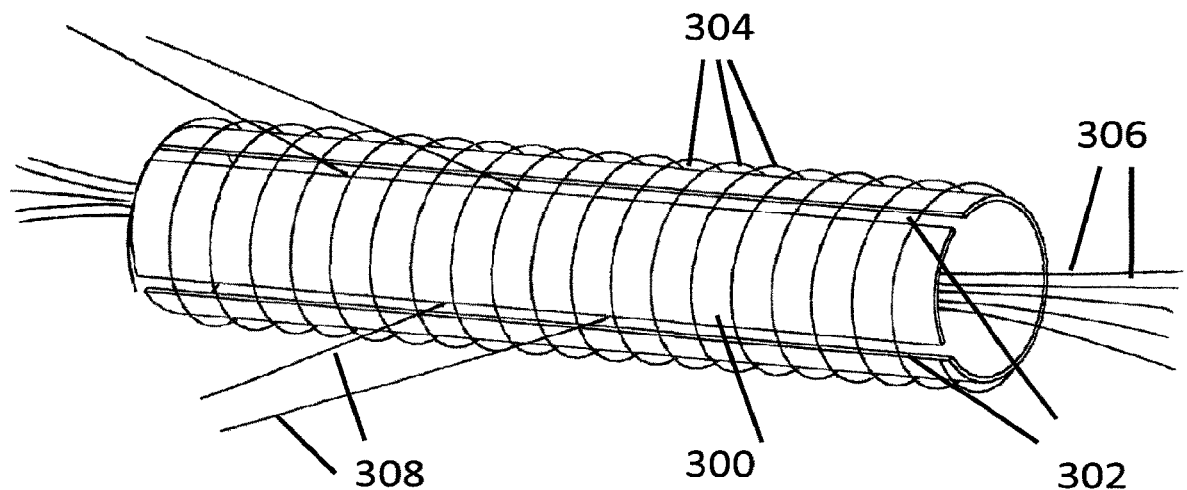

FIG. 3 illustrates a method by which the gap between two adjacent filaments is established in accordance with an exemplary embodiment.

Figure 4:
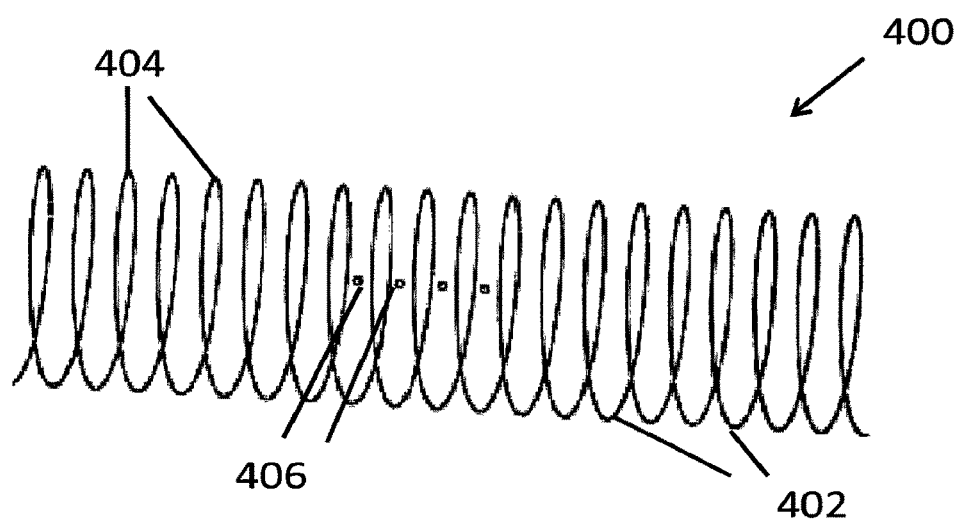

FIG. 4 illustrates contact point on the surface of a lead made using the method shown in FIG. 3 in accordance with an exemplary embodiment.

Figure 5:
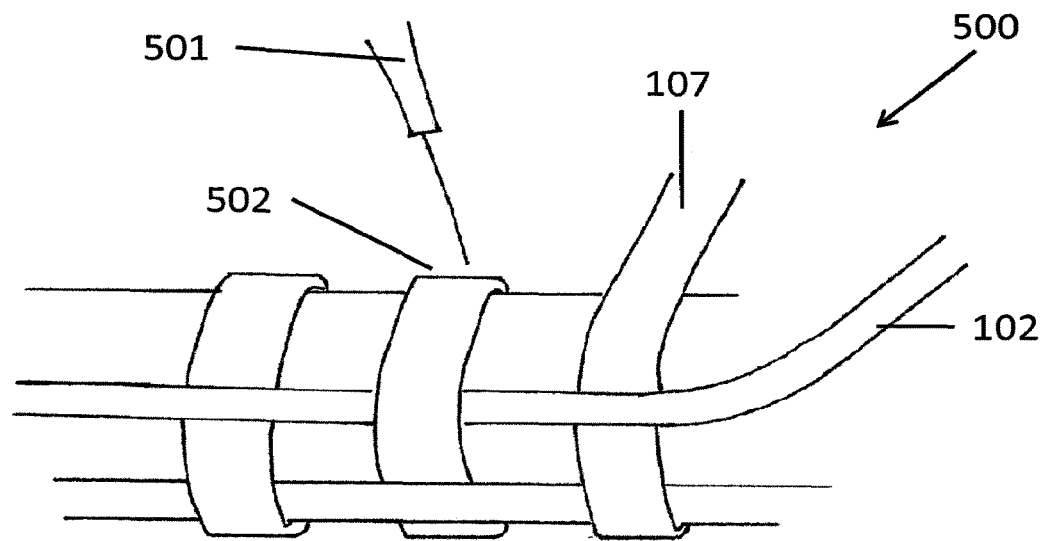

FIG. 5 illustrated a method by which action is inflicted on filaments during production process according to exemplary embodiment.

Figure 6A:
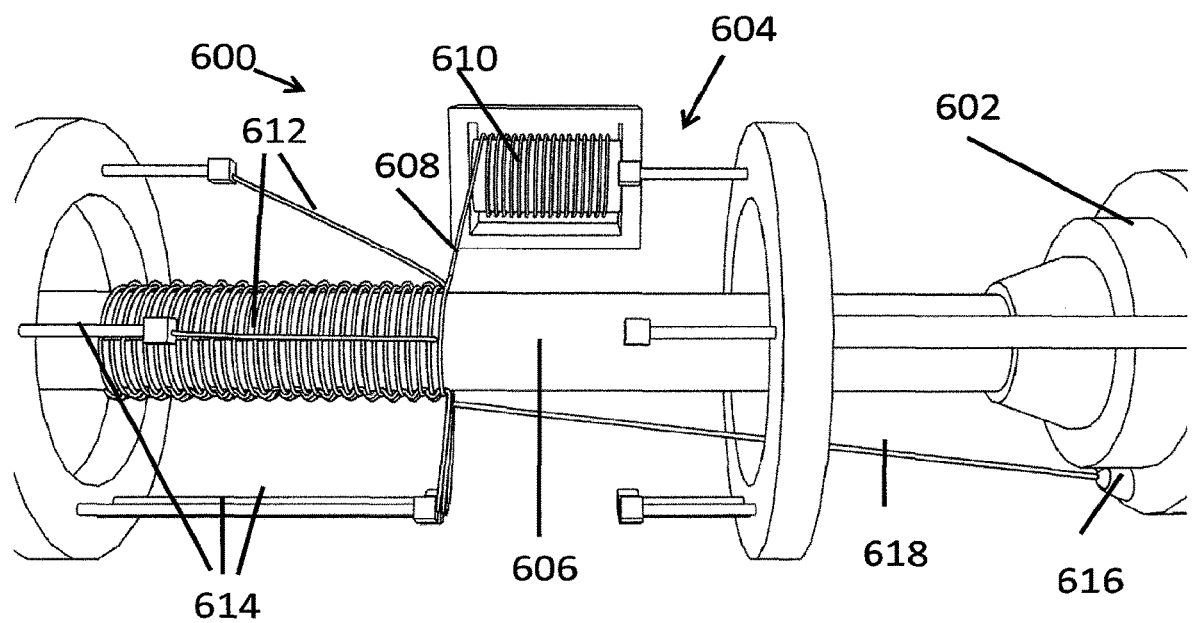

FIG. 6a schematically illustrates an apparatus for manufacture of an interlocked structure according to exemplary embodiment.

Figure 6B:
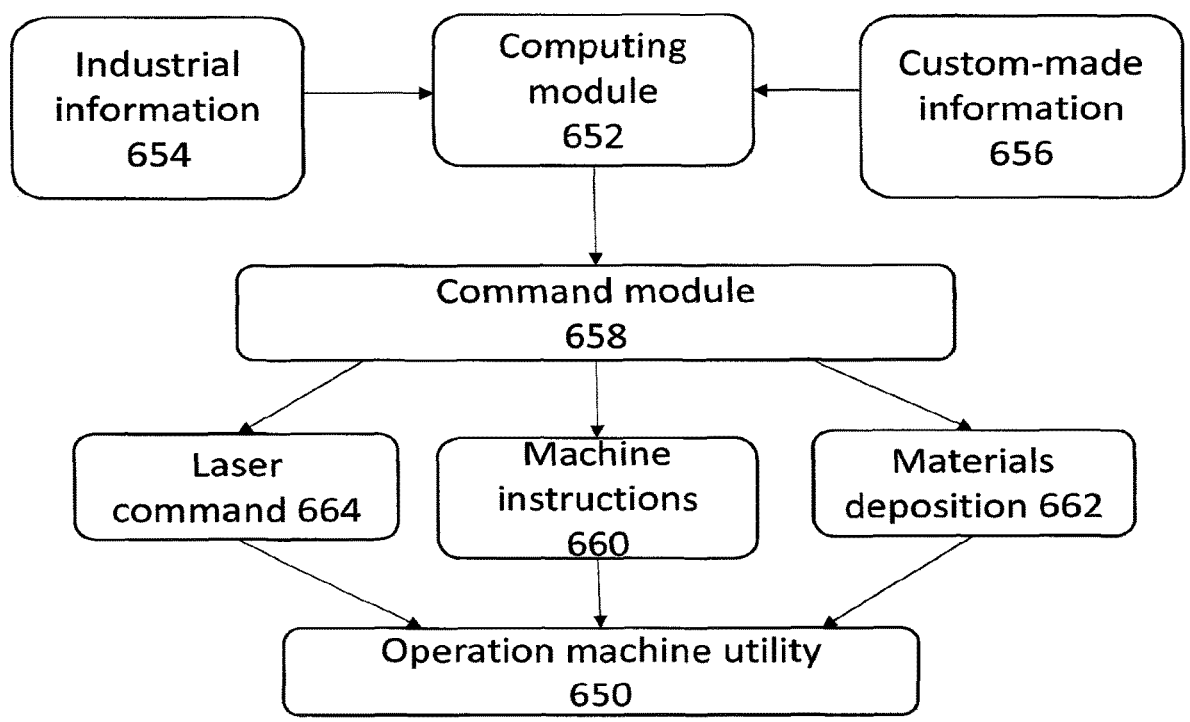

FIG. 6b depicts a block diagram of a method of manufacturing an electrode lead according to an exemplary embodiment.

Figure 7A:
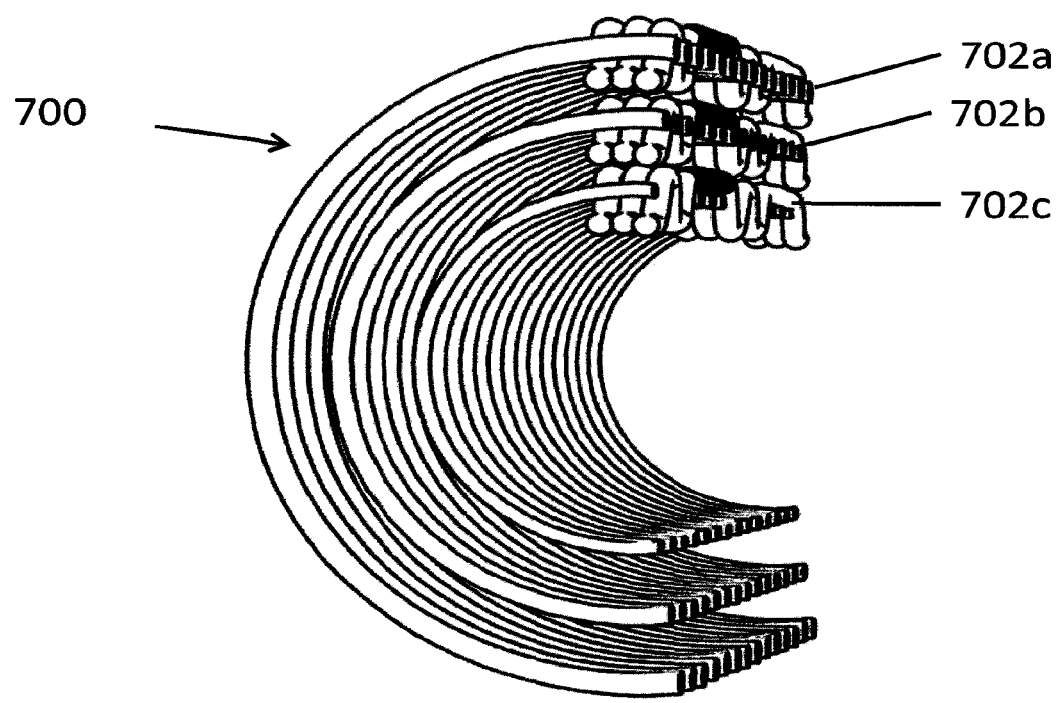

FIG. 7a illustrates a portion of multilayered lead according to an exemplary embodiment.

Figure 7B:
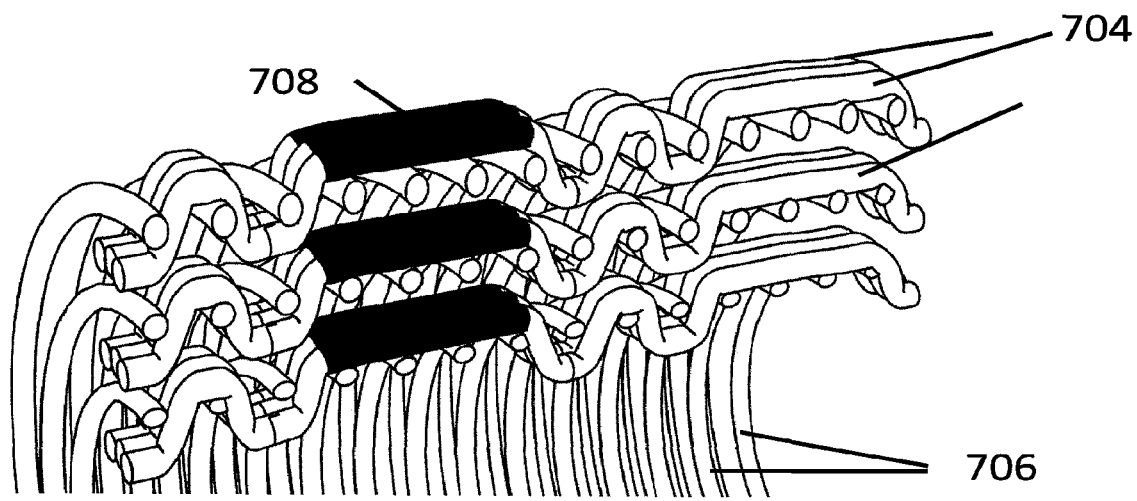

FIG. 7b is an enlarged portion of the layers in FIG. 7a.

Figure 8:
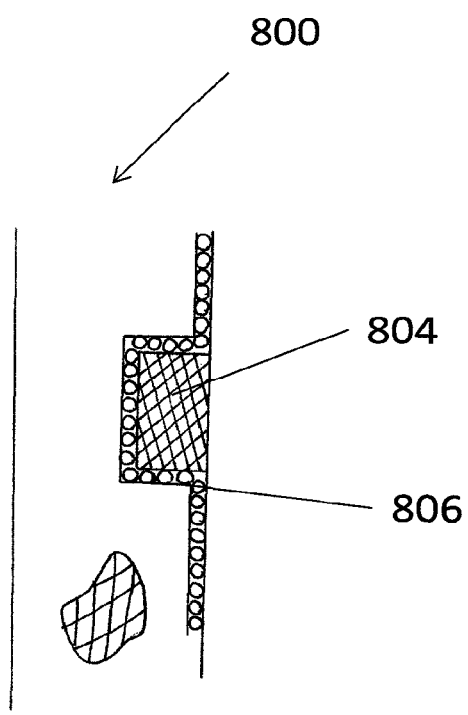

FIG. 8 illustrates a cross sectional view of an electrode lead through a contact according to an exemplary embodiment.

Figures 9A, 9B:
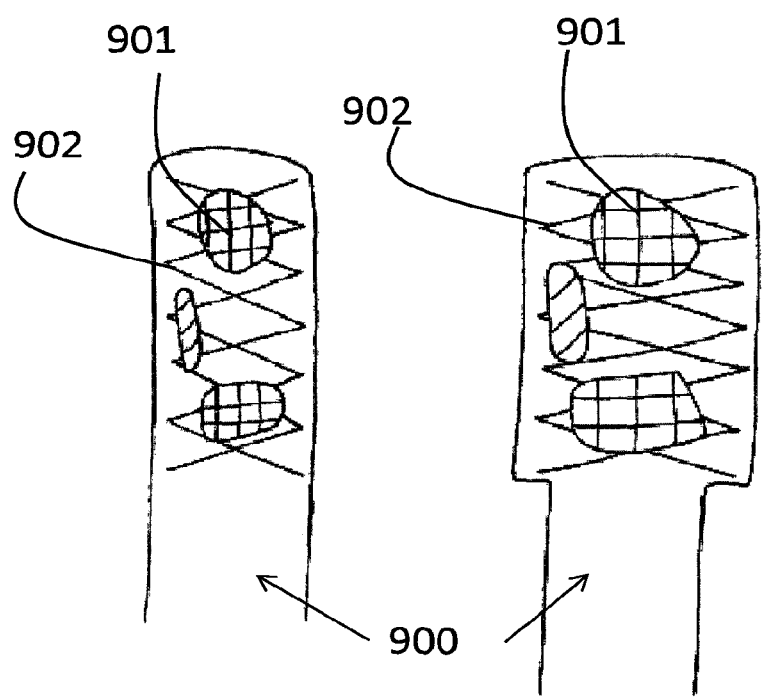

FIG. 9a illustrates a cross sectional view of a distal end of an electrode lead according to another exemplary embodiment.

FIG. 9b illustrates the cross sectional view of a distal end of the electrode lead shown in FIG. 9a after expansion.

DETAILED DESCRIPTION OF THE INVENTION

According to aspects and embodiments of the present invention, a lead for electrode and a method of producing the same are provided. The embodiments are aimed at constructing a lead made of a plurality of interlocked filaments bundled to form a lead with electrode contacts in its distal side that may be also custom made. The interlocked filaments can be manufactured by braiding, knitting, weaving, interwinding, entangling, meshing, or any other method by which the filaments are interlocked into a specific predetermined structure. Any other method by which filaments can be interlocked into a three dimension structure that can act as an electrode is covered by the scope of the present invention.

The lead can comprise two types of filaments organized in layers—fully nonconductive filaments and filaments made of conductive material coated by a nonconductive material. In order to form contact surfaces in the lead that are capable of transferring electrical signal in or out of the lead, a portion or a segment of the nonconductive coating is removed from the filament so as to expose the conductive material. A contact surface is a surface made of several adjacent exposed areas in several filaments positioned in the outer layer of the lead.

The size of the surface can be predetermined in accordance with the actual area in the body that is to be stimulated through the electrode so as to allow control of the flow of electric signals through the surface. Each individual contact can be in a different size than the other and all in accordance with the specific needs and requirements of the specific individual and condition to be treated.

It should be emphasized that forming contacts using exposed conductive portions of the filaments is a substantial advantage of the embodiments that will be disclosed herein after over prior art. The fact that the contacts are part of the filaments renders the contacts positional stability. e.g. the contacts cannot move relative the lead itself and cannot fall off: they are a part of the interlocked structure.

Another important feature of the disclosed lead is the directionality of the electrodes. Generally, the electrodes surface area is facing an axis substantially perpendicular to the elongated axis of the lead. In this way, there is full control of the area in the tissue to be stimulated or monitored for electric activity. As an example, in treating Parkinson disease, stimulating electrodes are positioned in deep brain tissues and are used to stimulate very specific tissues in a very specific therapeutic time window. Nowadays, as an example, ring electrodes are provided on a lead at several perimeters of the lead and the electric signal is symmetrically transmitted about the lead. Therefore, the electric field in not directed solely to the treated area, the flow of electrical signals all around the lead.

According to one aspect of the invention, since the size of the contact surface is fully controllable and can be very small, more than one contact can be provided on a certain perimeter about the lead. In this way, the electric signal is fully directed to the area to be treated without having signals that are directed towards unwanted areas.

Accordingly, reference is now made to the figures.

Reference is now made to FIG. 1a illustrating a schematic drawing of distal portion of a lead according to an exemplary embodiment. Distal portion 12 of a lead 10 is elongated and capable of reaching distal and deep tissues or other targets in the body. Relatively small contacts 14 are discretely distributed on the surface of the lead. The contacts 14 allow electric signals to flow through its surface in order to stimulate the adjacent tissue or in order to collect electrical signal, depending on the requirements. In order to observe the inner structure, a cross sectional view in the A-A plane is shown.

Reference is now made to FIG. 1b illustrating a schematic cross sectional view of the lead shown in FIG. 1a. The lead 10 shown in this figure has an empty core 18 through which guide wires or similar medical devices can be inserted. As mentioned herein before, the lead is made of interlocked network of filaments. In this schematic figure, the individual filaments are not shown. Interlocking possibilities to establish a 3D structure of a lead will be shown herein after. The filaments are mainly made of conductive wire coated with an isolating material. The bulk of the lead comprises interlocked nonconductive filaments. A portion of the nonconductive filaments can be filaments that are entirely nonconductive and a portion can be conductive filaments coated with nonconductive material. In order to form the electrode contact, the isolated nonconductive material is removed from a plurality of adjacent filaments (this issue will be elaborated herein after), to form a conductive mass 16 that acts as a 3D contact. The plurality of exposed filaments in one area of conductive mass 16 are isolated from each other in order to prevent short circuits between the filaments at the lead's distal end and to form one connector contact. The filaments are connected to each other at an electronic module in the proximal end of the lead so as to transfer the electrical signals from the contacts or collect the electrical information coming from the contacts. The electronic module is not shown in the figures and any module available in the art or specific module can be utilized without limiting the scope of the present invention.

The flow of electrical signals into and out from the conductive mass 16 is possible through the outer surface area 14 of the contact that is substantially aligned with the surface of the lead 10. The directionality of the electric signals formed in the contact is substantially determined by the outer surface area of the contact. The larger the conductive mass 16 is, the better the electrical properties of the contacts are (e.g. lower the impedance of the contact). Therefore, more current will flow through the surface area of the contact. This feature is also important in sensing and recording electrode leads since this feature renders the electrode lead with lower signal to noise ratio.

As mentioned herein before, the bulk of the lead is made of interlocked filaments made of isolated conductive wires and the conductive mass are areas where the isolated coating of the wires is being removed. Therefore, a possibility opens for a vast variety of structures to be produced.

Optionally and since the conductive masses are totally discrete and can be made of very small surface area size, it is possible to use several of the electrodes on the same lead as stimulating electrodes while other electrodes am being used as sensing electrodes. In this way, one can treat the tissue and at the same time receive feedback from the same or adjacent tissue without the need to employ two separate surfaces for electrode contacts on the same lead.

The filaments to be used for the electrode leads of the present invention are to be totally biocompatible with the body and made from materials that can be implanted within the body. As for the conductive core of the filament, conductive metals can be used such as stainless steel, platinum, titanium, tungsten, iridium, cobalt alloys, or combinations alloys. The isolation coating can be made of polymeric materials such as Parylene, silicones, polyethylene, polyvinylchloride, polyurethanes, polylactides. Other materials can be employed without limiting the scope of the present invention.

Reference is now made to FIG. 1c and 1d illustrating a schematic drawing of distal portion of an electrode lead and a cross sectional view, respectively, according to other exemplary embodiments. According to these examples, an electrode lead 20 has a plurality of 3D patterns of distinct and spaced apart regions 22 of conductive mass along the surface (FIG. 1c) and extend to within (FIG. 1d) the electrode lead 20. These patterns can be of various surface area shapes, while an important aspect is the directionality of the surfaces that can be predetermined and is directly linked to the lead circumference span of the contact. Generally, as the spam is lower and the surface area of the contact is smaller, the electrical properties of the contact are worsen (e.g. higher impedance); it is desired that the electrical properties of the contact will be within certain limits so as to compensate for this degradation and produce a contact that have appropriate electrical properties. According to one of the aspects of the present invention, the contact structure is made of a volume that contains conductive network of exposed segments of plurality of filaments so that the total surface area of the conductive elements that is in contact with the body tissue or body fluids is substantially equal to a surface area of a planar contact adapted to yield the same electrical property. For example, a highly used deep brain stimulation (DBS) electrode having a cylindrical contact with a length of 1.5 mm and a diameter of 1.27 mm yields an impedance (tested in laboratory) of around 500 Ohm, which is directly related to contact surface area which can be calculated as 6.123 mm^2 (external surface area of the contact). In order to produce a directional contact with a quarter external surface area and the same impedance, it is required that the total surface area of the contact mass altogether be equal to 6.123 mm^2. This is accomplished by producing a volumetric contact (conductive mass) with spread apart conductive filaments defining the required surface area.

Reference is now made to FIG. 2a-2e schematically illustrating several possible methods of weaving layered lead in accordance with exemplary embodiments. In order to form a lead, weaving of filaments in layers is preferably used. As mentioned herein before, weaving is one of the methods of interlocking the structure of the lead in accordance with embodiments disclosed herein. The filaments to be used can be of diameters as small as 8 μmeter; therefore, a lead can be produced with layers having width of about once or twice the diameter of the filaments. Using the method disclose herein, leads of relatively small diameter can be produced. As a comparison, using one of the new technologies, 3D printing, one can think of the possibility of building a lead of electrodes having a diameter in the range of 100 μmeter. Using the weaving technology may produce leads of much lower diameters that can be used for different application in a much accurate manner that can be established with today's leads.

A first simplified axial pattern is shown in FIG. 2a. Horizontal filaments 102 are running from left to right to establish a layer arranged about an elongated axis. Weaving filament 107 weaves the horizontal filaments 102 together in a weaving pattern that is fairly known in the weaving art. The width of the layer is twice the diameter of a filament in its maximum.

FIG. 2b illustrates another weaving axial pattern where the weaving filament 107 surpasses each time over two horizontal filaments 202 and one filament when passes bellow the horizontal filaments; and so forth. This pattern can be woven on the opposite side of the layer. The weaving filament 107 can surpass bellow two horizontal filaments 102 and immediately after pass above one horizontal filament 102. Any combination of these patterns can be accomplished. Also here, the width of the layer is twice the diameter of a filament in its maximum.

FIG. 2c illustrates a method by which another pattern can be achieved in two layers: a first layer with the simplistic woven structure shown in FIG. 2a is formed e.g. horizontal filaments 102 woven together by weaving filament 107, and another layer can be formed in the same manner; however, in the pattern shown in FIG. 2c, the two layers are interlocked together in occasional exchanging points 204. It can be seen that this pattern does not necessarily form an axial structure, but rather, a flat structure.

FIG. 2d shows another example of weaving profile that is axial. Horizontal filaments do not assume a horizontal path, instead they extend in a helical pattern 102 about an elongated central axis. Weaving filament 107 assumes a helical opposite pattern that interlocks with the helical pattern 102 of the horizontal filament. This woven structure can have stretching capability along the elongated central axis of the lead as well as more flexibility.

In FIG. 2e, a structure is shown that is based and combines the structures shown in FIGS. 2b and 2c. The horizontal filaments 102 establishes more than two layers, in this particular case, three layers, each can assume a certain pattern using the weaving filament 107. All layers can be interlocked while even distant layers can have exchanging points 207 as well as exchanging points 205 between adjacent layers. In the example shown in this Figure, if we follow a certain filament from the middle layer—filament 206—it can be seen that in exchanging point 205, which interlocks the upper layer and the middle layer, filament 206 will exchange layers from the middle layer to the upper one. Following further filament 206 to the right, the filament 206 is exchanging layers from the upper layer to the bottom layer in exchanging points 207.

Such exchanging points between the layers in the structure can form a lead having integrated layers that result in a 3D structure that is stronger and can endure high inflicted pressures. According to one aspect of the present invention, conductive masses are presented in the distal portion of the lead and occupies portions in the volume of the conductive mass as well as the surface area on the outer circumference of the lead. In case exchanging points are to be used, one should make sure when designing the layers, that each filament can have one exposed area with conductive characteristic, no matter if the filament is travelling among the layers from the surface are to the volume of vice versa.

Many other patterns can be produced using the methods depicted in this disclosure. It should be understood that any pattern that can be produced according to the methods described herein and other methods known in the art are covered by the scope of the present invention and by no means, the patterns shown herein limits the scope of the present invention.

It should be mentioned that all those patterns as well as other patterns are formed on a supporting frame or using supporting elements that are not shown in these figures and at least some will be shown in exemplary embodiments herein after.

One of the advantages of the method by which the 3D structures are built from the filaments as disclosed herein is the possibility to determine and control the gaps between the woven filaments. The gaps between the filaments can be equal all through the lead and can be different in different areas of the lead. As an example, the gaps between filaments can be larger in the proximal portion of the lead and smaller in the distal portion, where the conductive masses are formed. The gaps between the filaments render strength and stability to the lead as well as to the conductive masses having a surface area on the perimeter of the lead. Moreover, the gaps between the filaments increase the flow of electrical signals in and out from the conductive mass and basically assist in increasing the effective surface area of the contact without decreasing its directionality In order to form a stable and strong enough 3D structure, the gaps between the filaments should be controllable. In accordance with the method of the present invention, total control of the manufacturing process is achieved as will be explained herein after.

Reference is now made to FIG. 3 illustrating a method by which the gap between two adjacent filaments is established in accordance with an exemplary embodiment. It was already mentioned that supporting frames or structures are facilitating the methods by which a 3D structure is built. Supporting hollow cylinder 300 is provided with a slotted opening 302 that passes through the elongated axis of the cylinder connecting the hollow of the cylinder and its outer part. The supporting cylinder is an insert 300 that is assisting in establishing an axial built up of a pattern similarly as disclosed herein in FIGS. 2a and 2b. The layers are built on the cylinder 300, each after the other, as needed using the filaments. In this case, the gaps between the weaving filament 304 are considered. Along the longitudinal axis of the cylinder, a slot 302 is maintained, wherein the slot is made to be very thin so as to allow a filament to pass through it. Within the hollow in the cylinder, a group of filaments 306 is extending through both ends of the cylinder. The length of the insert can vary.

During weaving of the weaving filament 304, one or more filaments 308 accommodated within the hollow are being pulled through the slot and in opposite direction to the advancement of the weaving filament. After each winding of the weaving filament 304 or after several windings, a filament 308 is pulled from within the hollow and compresses the weaving filament backwards and towards the preceding winding of the filament. Using this embodiment, the windings of the weaving filaments are fully compressed one onto the other with a gap that can be determined by the intensity of the pulling or compressing action of the filament 308.

Optionally, pins or other elements can be positioned in a predetermined manner on the outer surface of the cylinder in order to form predetermined gaps between adjacent filaments.

Optionally, slotted structure can include plurality of slots, or slots that does not necessarily run parallel to the lead axis, the purpose of these slots is to determine the location on the lead circumference where the weaved internal filament protrude. In addition, interlocking the filaments together will yield a final cross section that suits the cross section of the slotted structure, one of the reasons being that all the internal filaments are contained within the slotted structure and protrude only when they turn during the weaving.

The ability to control the gaps between the filaments can assist in cases, as an example, in which a 2D structure is being built up. There are many cases in which a lead of electrodes should correspond to a certain bodily part in a human, such as in retinal prosthesis, as an example. Although the retina is a 2D structure as well, it forms a 3D structure due to its curvature characteristic. In order to form such 3D structure, a 2D structure such as the one shown in FIG. 2c is built with gaps that then can assist in curving the structure to a 3D structure.

It should be added that curving the flat structure can be performed in other ways without limiting the scope of the invention. In another way, the layer can be weaved flat, after which it can go through certain processing that can deform the layer into its three dimensional final structure.

Optionally, another way is to weave the flat lead from multiple layers that are being deformed by heat. The lead is being heated using heat images such as holographic laser or holographic JR mages that are projected on the lead. The lead then assumes a final shape from the image according to a desired final form. This also can be done in an iterative manner where a heating image could be projected on the lead made of weaved layers that causes a slight deforming. Then, another image can be projected to cause another slight deformation. This processes is repeated until the final desired shape is assumed. Other methods of deformation are possible.

Going back to FIG. 3, it is also possible to form contact surfaces using filaments 308 that am left protruding from the structure of the lead after winding the weaving filament 304. In this case, the filaments that are used as compressing filaments 308 has to be made of conducting wire coated with an isolating material. Cutting the filaments form contact points on the surface of the lead.

Reference is now made to FIG. 4 illustrating contact points on the surface of a lead made using the method shown in FIG. 3 in accordance with an exemplary embodiment. Lead 400 is produced using the method explained in connection to FIG. 3. From convenience reasons, only the weaving filament 402 is shown and only one layer is presented. The horizontal filaments are not seen. Relatively constant distance gaps 404 are provided between the windings of the weaving filament 402. As explained, the compressing filaments that according to some features of the method are protruding from the surface are cut so that their inner conductive cross section 406 is exposed on the surface of the lead 400. Those contacts can be as small as the diameter of the conductive core of the filament or of several such cores.

According to the method of the present invention, the contact masses that form the electrodes in a lead are made by removal of the nonconductive coating of the filament and exposing the conductive material. One of the methods of doing so is to ablate the nonconductive material of the filament using a laser beam. This method can ne employed for various other actions that should be inflicted onto the filament.

Reference is now made to FIG. 5 illustrating a method by which action is inflicted on filaments during the building process according to exemplary embodiment. Actions that can be inflicted onto the filaments during processing are actions such as filament cutting, gluing, welding, ablating, materials depositions or injecting isolation materials such as gels, glues or polymers examples for the purpose of controlling conductivity. The method as shown in FIG. 2a is employed and horizontal filaments 102 are interlocked with weaving filament 107. This is performed on a support rod 500. As an example, a laser head 601 is provided and connected onto a machine such as a weaver (not shown in this figure). Laser head 601 is sending a laser beam 602 according to a premeditated program so as to ablate the nonconductive material of the conductive wire or the energy suffice for cutting the filament so as to expose its conductive core. In the same manner, glue, insulating gel or other materials dispenser injection needle can be provided to the machine, wherein the dispenser is capable of injecting required amounts of glue to adhere the filaments or insulting gel to form an insulation area within the lead. Similarly, welding can be inflicted onto the filaments. In cases where glue or insulating material is dispensed onto the structure, an additional laser beam or lighting can be provided to the production machine so as to activate and cure the glue over the filaments in precise places.

Due to the extreme accuracy of ablation of the nonconductive material off the conductive core of the filaments during processing and as mentioned before, relatively small electrodes can be produced and in specific needed areas of the lead that correspond the need of treatment. As indicated herein before, in the example of the Parkinson disease, it is extremely important to be able to direct the electrical signals to very specific areas in the patient's brain tissue. As the electrode produced according to the method disclosed is very small and can be fabricated in any area of the lead, it can be custom made in a size and location that is specific to the treatment of a specific patient. These features renders the ability to place mom than 1-2 contacts so as to significantly increase the resolution of the treatment. This feature is not presented by any of the electrodes that are being used in the art or disclosed.

According to another aspect of the invention, a system is provided that is configured to allow manufacture of the interlocked structure.

Reference is now made to FIG. 6a schematically illustrating an apparatus for manufacture of an interlocked structure according to exemplary embodiment. The apparatus 600 comprises a command module 602 that is programmed with at least one weaving program, and a weaver 604 that is operationally coupled to the command module 602. The command module 602 controls the operation of the weaver 604 as well as the program by which it weaves the 3D structure. The command module 602 can be connected or integrated with a computing apparatus or module that can be provided with a plurality of programs to produce electrode leads of common use, there may be also a default program. The command module 602 or integrated computing apparatus can also be provided with a predetermined program that is built for a specific use and for a specific patient. Each patient may have different physical characteristics and therefore, producing specific lead for a specific patient can enhance the treatment in a significant manner.

The command module receives instructions from dedicated software that determine characteristics of the structure to be built. The characteristics to be determined are characteristics such as: the pattern or patterns to be used, type of filaments, number of layers, interlocks between the layers, the amount and size of contacts, the gap between the filaments, which filaments are to be used, isolation added to the contact, scan of a specific patient from which certain parameters should be extracted, application of isolating material, type of electrodes, etc. In accordance with the method of manufacturing the lead of the present invention, it should be emphasized that the process is to be fully computerized so that industrial electrode leads as well as custom-made electrode leads can be easily designed and manufactures using the dedicated software that instruct the manufacturing machine.

The weaver 604 has a cylindrical core 606 upon which the filament 608 is wound. A bobbin 610 provides the filament that is engaged with the cylindrical core 606 that rotates to receive the filament. Horizontal filaments are placed in their positioning using several arms 614 that are arranged on both sides of the cylindrical core 606, substantially parallel to the core, and around it. In order to simplify the figure, only few arms and even fewer horizontal filaments are shown, however, the number of arms around the cylindrical core can be very high and the number of arms that will be engaged in the production of a certain electrode lead is dependent on the amount of horizontal filaments that is needed for a certain lead. Each arm has an opposite arm on the other side of the cylindrical core 606. The arms 614 are extendable and each arm can hold an end of one horizontal filaments at its free end. The movement of the arms is controlled by the program in the command module 602 that determines if a certain horizontal filament that is engaged with the right arm, as an example, will be covered by the weaving filament 608 as the cylindrical core 606 rotates, whereas filament engaged with the left arm will not be covered and will be placed above the weaving filament. Thus, an interlocked structure of the filaments is formed. The possibilities of the patterns is vast and is fed to the program in the command module 602.

As indicated herein before, the filaments are nonconductive, however, a substantial number of the filaments are made of a conductive core or wire with an isolating coating. In order to form the electrodes and their contact surfaces, a portion of the nonconductive coating is to be removed. For this purpose, the weaver 604 preferably comprises a high power laser 616 that is capable of ablating the nonconductive coating from the filament so as to expose the conductive material that can act as an electrode. Again, the areas in which the nonconductive coating is removed are predetermined according to the active program fed to the command module 602. Preferably, the laser 616 is affixed to the cylindrical core 606, or at least rotates relative to the arms 614. In this way, as the cylindrical core 606 rotates, various filaments around the circumference of the cylindrical core can be exposed to a laser beam 618 from the laser 616.

Optionally, more than one laser is provided to the apparatus 600 that may be synchronized with the other laser or may be independent or work as a backup.

Optionally, when one of the arms 614 holds a horizontal filament 612 that is programmed to be exposed to a laser beam, they are positioned at the time of the exposure close to its placement on the cylindrical core 606. Thus, the filament in this position is essentially perpendicular to the cylindrical core and is the only filament that is positioned in the path of the laser beam. In this way, there is minimal exposure if any, of other filaments to the beam and the exposed area on the filament is of minimal and accurate size and consistently defined.

It is noted that in FIG. 6, the laser 616 is positioned on the right hand side of the cylindrical core 606 and therefore, the filaments are being exposed on the side of the filament that face the cylindrical core 606. The exposed or conductive area of the filament will be in this case on the internal side of the layer that is being built. In some embodiments, the laser can be positioned on the left hand side of the core and in this way, the exposures are on the exterior side of the formed layer. Optionally, there are lasers on both sides of the core, allowing contacts to be formed on both the interior and the exterior side of the interlocked structure.

Optionally, a dispenser similar to the one disclosed and described in regard to FIG. 5 can be added to the apparatus 100 so that during the processing of the electrode lead, glue or isolating materials can be placed on the filaments or woven structures.

Optionally, other means can be used to remove the isolated coating and expose the conductive materials from inside. Any other means is covered by the scope of the present invention and by no means limits the invention.

After one layer is being formed on the cylindrical core, it is optional to form another layer on top of it. For this purpose, the interlocked layer may be left in the weaver 604 and another layer may be woven on top of it, to make a multilayer interlocked lead. Several layers may be formed one of top of the other in this way. The top layer or the interior layer may be left unexposed on the interior or exterior side to help isolate the lead from tissue that should not be stimulated or sensed (according to the tissue and application).

Upon completion of the weaving process, the interlocked structure that comprises the lead with conductive mass having contacts on the lead's surface is removed from the apparatus 600, and connected to a suitable electrical circuit so that the conductive mass can be used as electrodes through which electrical signals are transferred.

Reference is now made to FIG. 6b depicting a block diagram of a method of manufacturing an electrode lead according to an exemplary embodiment. As mentioned herein before, in accordance to one of the aspects of the present invention, a production machine 650 is producing an interlocked structure made of filaments. The production machine 650 can be a weaving machine, a sewing machine, braiding machine, or any other machine that is capable of interlocking filaments into a structure that is predetermined. In order to predetermine the structure of the electrode lead to be produced in the machine, a computing module 652 is provided that can calculate information received from several sources and transfer the results to a command module 658 that, in turn, activate the machine 650 to produce the resulting product according to the commands. The command module 658 can instruct the machine to operate in a certain manner, to move elements from place to place according to a certain program so as to interlock the filaments in a predetermined manner. In addition, the command module 658 also provide instructions to the laser command 664 so as to ablate the filaments and expose the conductive material in a predetermined area of the filament that will be placed exactly in a place that can be in the conductive mass (surface or volume). In a similar manner, should materials be disposed in predetermined areas of the 3D formed structure, instructions from the command module will be delivered for this feature as well 662.

Optionally, some of the units can work together or being integrated to within one single unit or module.

The program that is calculated in the computing module 652 receives information from at least two sources: information coming from known and predetermined structure programs known in the industry 654. Another source is the custom-made source 656 from which the calculating module 652 should produce a custom-made electrode lead. Examples of the information needed here can be information on the resolution needed for the electrode, the size of the surface of the contact directional to the tissue and the whole surface of the exposed areas, contact mass electrical properties needed, flexibility of the lead etc.

Reference is now made to FIGS. 7a and 7b illustrating in details a portion of multilayered lead according to an exemplary embodiment. FIG. 7a illustrates a portion of a lead made using an apparatus such as the one disclosed in FIG. 6. The portion of the lead 700 comprises 3 layers, 702a, 702b, and 702c, wherein 702a is the outermost layer of the lead. The layers shown in the Figure are very simplistic so as to be able to understand the structure. In FIG. 7b, the structure of the filaments in the layer is better seen. Plurality of horizontal filaments 704 are interlocked with weaving filaments 706. As explained before, a portion of the horizontal filament is being ablated before it is being interlocked into the structure. As a result, a portion of the horizontal filament 704 is a conductive wire 708. In this specific case, one can see that all layers are of the same organization of filaments and the portion that is exposed, conductive wire 708, is of the length of substantially four times the filament's diameter since this portion surpasses 4 adjacent weaving filaments 706.

The conductive wire 708 shown in FIG. 7b that is positioned on the most outer layer 702a correspond to the surface area of contacts 14 shown in FIG. 1b and the conductive wires in the layers beneath it correspond the conductive mass 16 shown in the same FIG. 1b.

It should be noted that the interlocked structures formed using the method described herein are flexible. This renders the ability of the distal portion of the electrode lead to conform to the target area in a better way than existing electrodes. The interlocked structure made of filaments in accordance with the embodiments of the present invention also has longer fatigue life because for similar deflections and motions the electrode lead is inflicted with. The stress levels for the smaller structure is greatly lessened. In addition, each filament is redundant allowing for continuing functionality even if it breaks. The interlocked structure allows for a larger amount of electrode surface area to be exposed to the target area, thus lowering current densities at the electrode/tissue interface.

As mentioned herein in regard to FIG. 5, a dispenser can be added to the apparatus to add adequate materials during the manufacturing process.

Reference is now made to FIG. 8 illustrating a cross sectional view of an electrode lead through a contact according to an exemplary embodiment. An electrode lead 800. A conductive mass 804 made of a plurality of interlocked and exposed filaments is provided. The circumference of conductive mass 804 is provided with a plurality of isolation spots 806 that can be provided also on the circumference of the electrode lead 800 itself. This feature of providing isolation spots is possible due to the method in which the structure is manufactured using a machine that interlocks the filaments while during the processing of the filaments, materials can be added to the structure as well as actions inflicted on them. Due to the fact that the procedure is fully computerized, the exact filament or structure onto which the material should be dispensed is located and therefore, the positioning of such isolation spots is accurate.

The need of the isolation spots arises from the structure of the electrode lead that comprises interlocked filaments. As already indicated, interlocked filaments that comprises the conductive mass are having their conductive parts exposed. When the electrode lead is in the body, the liquids of the body are entering the structure and may cause the electrical signals to pass internally within the lead. Placing isolated spots between the contacts and the nonconductive areas prevents this phenomena.

Another use of such spots can be to form conductive paths between two distinct contacts. This may be desirable when a return current is needed. For example, in cases where some of the lead contacts are connected to different current sources at the lead proximal end, if the produced total current is not equal to zero, one of the lead contacts can internally be connected to a return electrical ground that act as a sink for all the extra current.

Reference is now made to FIGS. 9a and 9b illustrating a cross sectional view of distal end of an electrode lead according to another exemplary embodiment. The distal end of the lead 900 is enclosing a stent 902 that is capable of expanding. Conductive mass 901 are provided also at the distal end. Such electrode lead can be beneficial during lead implantation since during implantation, the lead diameter should be small in order to be easily and safely inserted while after implantation to the correct target place, the distal end of lead can expand in its diameter, as an example, and can be enlarged as and when required. In deep brain stimulation electrode, as an example, it can be desired that the lead diameter during implantation be less than 0.8 mm and after implantation to be about 1.3 mm. In this example, the network of interlocked structure filaments of the lead is formed to be stretchable along the lead's elongated axis and enlarged in diameter as described in earlier embodiments of the present invention. This exemplary electrode lead allows the implantation of the lead when it is in its minimal diameter at the distal end, while once the lead is implanted, the distal end will be increased by forcing the stent to gain its longer diameter as shown in FIG. 9b. It can also be seen that the surface area of the lead increases when the distal end diameter is increased. It is also possible to keep the total surface area of the contact unchanged during enlargement.

It should be noted that other mechanisms of expansion such as a balloon can be used to enlarge the electrode lead diameter without limiting the scope of the present invention.

It should be noted that since the electrode leads of the present invention are to be implanted in the body, the materials from which they are comprised should accord the MR conditionals and withstand MRI environment. Moreover, since the electrode lead of the present invention is made of interlocked filaments passing along the lead's axis while other configuration running in different directions then it will be possible to create filaments configurations that are electromagnetically compatible, this is accomplished by for example creating filaments with conductive cores running in special loops in opposite directions that eliminate interference with electromagnetic fields such as MR at the same time reducing radiated transmission from the lead.

Optionally, regular ring or other electrodes can be combined within the structure of the electrode lead according to the present invention without limiting the scope of the invention.

Optionally, if sensing and stimulating electrodes are to be used together, it is possible to combine the two in a single conductive mass—several filaments will be used for the sensing electrodes and the other filaments will be used for the stimulating electrodes.

It should be emphasized that although weaving of filaments was chosen to be an exemplary embodiment for interlocking filaments in this disclosure, it should be understood that other interlocking methods are in the scope of the present invention and by no means limits the scope of the invention.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

The scope of the present invention is defined by the appended claims and includes both combinations and sub combinations of the various features described hereinabove as well as variations and modifications thereof, which would occur to persons skilled in the art upon reading the foregoing description.

What is claimed is:

1. A method of producing an interlocked structure comprising:
    providing a machine capable of interlocking a plurality of filaments into said interlocked structure;
    providing a plurality of filaments, at least one of said filaments comprising a conductive core coated with a nonconductive coating;
    interlocking said plurality of filaments according to a premeditated program to form said interlocked structure; and
    inflicting an action onto at least a portion of at least one of said plurality of filaments during interlocking process, wherein said step of inflicting an action comprises at least one of filament cutting, gluing, welding, ablating and deformation by heat using heat images being projected onto said interlocked structure.

2. The method as claimed in claim 1, wherein said interlocked structure is a 3D structure.

3. The method as claimed in claim 2, wherein said interlocked structure is a 3D electrode structure.

4. The method as claimed in claim 2, wherein said interlocked structure is a 2D electrode structure.

5. The method as claimed in claim 1, wherein said interlocked structure is a 2D structure.

6. The method as claimed in claim 1 and wherein said step of inflicting an action onto at least a portion of at least one of said plurality of filaments comprises ablation of said nonconductive coating from at least a portion of at least one of said plurality of filaments using a laser beam.

7. The method as claimed in claim 1 and wherein said step of inflicting an action onto at least a portion of at least one of said plurality of filaments comprises at least one of filament cutting, gluing, welding, ablating.

8. The method as claimed in claim 1 and further comprising providing a dispenser capable of directing material towards at least a portion of at least one of said plurality of filaments during interlocking of said plurality of filaments.

9. The method as claimed in claim 8 and wherein said dispenser is configured to dispense materials selected from the group of glue, gel, polymer and isolating material.

10. The method as claimed in claim 1 and wherein said interlocked structure is a flat lead, and wherein said step of inflicting an action onto at least a portion of at least one of said plurality of filaments comprises deformation by heat using heat images being projected onto said interlocked structure.

11. The method as claimed in claim 1 and wherein said interlocked structure is an electrode lead with a circumferential surface, the electrode lead extending along a longitudinal axis and comprising at least one volumetric 3D distinct conductive mass, wherein said at least one volumetric 3D distinct conductive mass made of said plurality of interlocked filaments arranged in multiple layers, said layers are disposed radially outwardly from said longitudinal axis and include external and internal layers; and wherein at least one of the filaments in said 3D conductive mass has an exposed conductive core and wherein a portion of the filaments with the exposed conductive core is disposed on at least one of said internal layers.

12. The method as claimed in claim 1, further comprising the step of providing a computing module and programming the computing module to instruct the machine according to a predetermined pattern of the interlocked structure, wherein said programming the computing module comprises: providing parameters from which characteristics of the interlocked structure are established, or providing characteristics of the electrode structure from which parameters of said interlocking the plurality of filaments are established.

13. The method as claimed in claim 12, and wherein said electrode lead further comprises a 3d pattern of spaced-apart regions along or within the electrode lead, each one of said spaced-apart regions is a network of spaced-apart conductive segments determining together critical parameters of: directionality of the region and electrical property of the region.

14. The method as claimed in claim 12, and wherein the electrode lead is provided with at least one insert residing in between layers that comprise the electrode lead, and wherein filaments are passed through at least one slot in the insert in an angle relative to an elongated axis of the electrode lead, wherein the filaments are optionally cut at the circumferential surface.

15. The method as claimed in claim 1, wherein the interlocking includes one of the following methods: braiding, knitting, weaving, interwinding, entangling, or meshing.

16. The method as claimed in claim 15, and wherein said parameters comprise a scan of a specific patient from which certain parameters are extracted.

17. The method as claimed in claim 1, wherein said machine is provided with a hollow cylinder onto which the interlocked structure is interlocked, wherein said cylinder is optionally provided with at least one slot through which additional filaments can be transferred from the hollow cylinder to outside the interlocked structure.

18. The method as claimed in claim 1, further comprising:
a step of pulling the additional filaments from the hollow cylinder through the slot in a direction opposite to the direction of the interlocking of said plurality of filaments, and
optionally cutting the additional filaments adjacent to the circumferential surface.

19. The method as claimed in claim 1 further comprising the step of providing a laser head capable of directing a laser beam towards at least a portion of at least one of said plurality of filaments during interlocking.

20. The method as claimed in claim 1, wherein the action is inflicted in a predetermined manner.

21. The method as claimed in claim 1, wherein said action is inflicted onto at least said portion of at least one of said plurality of filaments before interlocking thereof into said interlocked structure.

* * * * *